United States Patent
Lemerovich

(10) Patent No.: US 10,265,103 B2
(45) Date of Patent: Apr. 23, 2019

(54) SPINAL PROSTHESIS WITH ADJUSTABLE SUPPORT ELEMENT

(71) Applicant: Premia Spine Ltd., Netanya (IL)

(72) Inventor: Ilan Lemerovich, Herzliya (IL)

(73) Assignee: Premia Spine Ltd., Ramat Poleg (IL)

( * ) Notice: Subject to any disclaimer, the term of this patent is extended or adjusted under 35 U.S.C. 154(b) by 118 days.

(21) Appl. No.: 15/240,070

(22) Filed: Aug. 18, 2016

(65) Prior Publication Data

US 2018/0049778 A1  Feb. 22, 2018

(51) Int. Cl.
*A61B 17/70* (2006.01)

(52) U.S. Cl.
CPC ...... *A61B 17/7043* (2013.01); *A61B 17/7011* (2013.01); *A61B 17/7032* (2013.01); *A61B 17/7049* (2013.01); *A61B 17/7052* (2013.01)

(58) Field of Classification Search
CPC .................................. A61B 17/7049–17/7052
USPC ................................................ 606/250–253
See application file for complete search history.

(56) References Cited

U.S. PATENT DOCUMENTS

| 6,083,226 A * | 7/2000 | Fiz ..................... A61B 17/7035 606/250 |
| 2009/0093848 A1* | 4/2009 | Neary ................ A61B 17/7052 606/277 |
| 2009/0299411 A1* | 12/2009 | Laskowitz ......... A61B 17/7008 606/246 |
| 2011/0282391 A1* | 11/2011 | Dall .................... A61B 17/705 606/278 |

* cited by examiner

*Primary Examiner* — Nicholas J Plionis
(74) *Attorney, Agent, or Firm* — Dekel Patent Ltd.; David Klein

(57) ABSTRACT

A spinal prosthesis includes first and second spinal attachment members attachable to first and second spinal structures, respectively. One or more adjustable stopper elements are assembled on one or both of the first and second spinal attachment members. The one or more adjustable stopper elements are formed with a bore through which either of the first and second spinal attachment members is slidable. The one or more adjustable stopper elements include structure that limits relative movement between the one or more adjustable stopper elements and the spinal attachment member on which the one or more adjustable stopper elements are mounted.

13 Claims, 11 Drawing Sheets

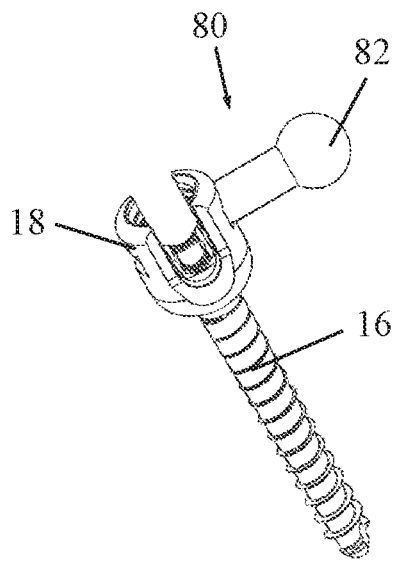
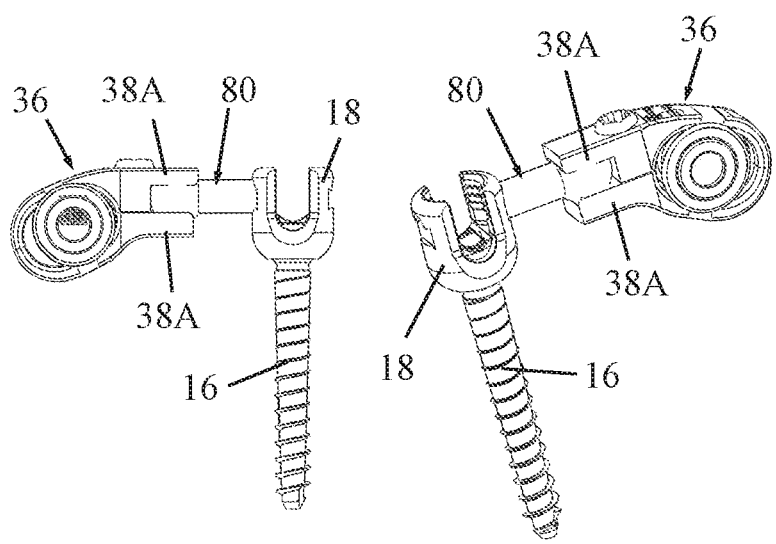
FIG. 6A
FIG. 6B FIG. 6C

SPINAL PROSTHESIS WITH ADJUSTABLE SUPPORT ELEMENT

FIELD OF THE INVENTION

The present invention is generally related to apparatus and methods for spinal prostheses, and particularly to a spinal prosthesis with an adjustable stopper element.

BACKGROUND OF THE INVENTION

U.S. Pat. No. 7,604,652 to Arnin describes a spinal prosthesis that includes first and second spinal attachment members attachable to first and second posterior portions of spinal structure, respectively. The first and second posterior portions are adjacent superiorly-inferiorly to one another. A connector element is attached to the first spinal attachment member. The second spinal attachment member includes an interface portion that passes through an elongate aperture formed in the connector element so as to permit rotational and translational movement of the second spinal attachment member with respect to the connector element.

The elongate aperture defines limits of movement of the second spinal attachment member with respect to the connector element. The interface portion of the second spinal attachment member is integrally formed with abutments spaced from the end faces of the elongate aperture. The abutments define limits of movement of the interface portion. The end faces and the abutments may have curved contours that mate with each other.

Since the abutments are part of the interface portion of the second spinal attachment member, the position of the abutments is basically the same for all patients. This is disadvantageous because the anatomy of patients can vary widely; if the abutments are not placed correctly with respect to the particular anatomy, the abutments can lose their effectiveness, or worse, can interfere with the correct functioning of the prosthesis.

Another disadvantage is that the spinous process can interfere with the abutment members, which means a laminectomy must be performed to remove the spinous process.

SUMMARY OF THE INVENTION

The present invention seeks to provide a novel spinal prosthesis, as is described more in detail hereinbelow, which improves upon the prosthesis U.S. Pat. No. 7,604,652. In the present invention, instead of fixed abutments, an adjustable stopper element is provided whose position is adjustable to suit any anatomy and there is no need to perform a laminectomy.

There is thus provided in accordance with an embodiment of the present invention a spinal prosthesis including a first spinal attachment member, a second spinal attachment member, and one or more adjustable stopper elements assembled on one or both of the first and second spinal attachment members, the one or more adjustable stopper elements being formed with a bore through which either of the first and second spinal attachment members is slidable, the one or more adjustable stopper elements including structure that limits relative movement between the one or more adjustable stopper elements and the spinal attachment member on which the one or more adjustable stopper elements are mounted.

BRIEF DESCRIPTION OF THE DRAWINGS

The present invention will be understood and appreciated more fully from the following detailed description, taken in conjunction with the drawings in which:

FIG. 6A is a simplified pictorial illustration of a spherical-head, superior-inferior link member attached to a pedicle screw head, in accordance with another non-limiting embodiment of the present invention;

FIGS. 6B and 6C are simplified side-view and pictorial illustrations, respectively, of the spherical-head, superior-inferior link member of FIG. 6A attached to a crossbar connector element;

DETAILED DESCRIPTION OF EMBODIMENTS

Figure 1A:
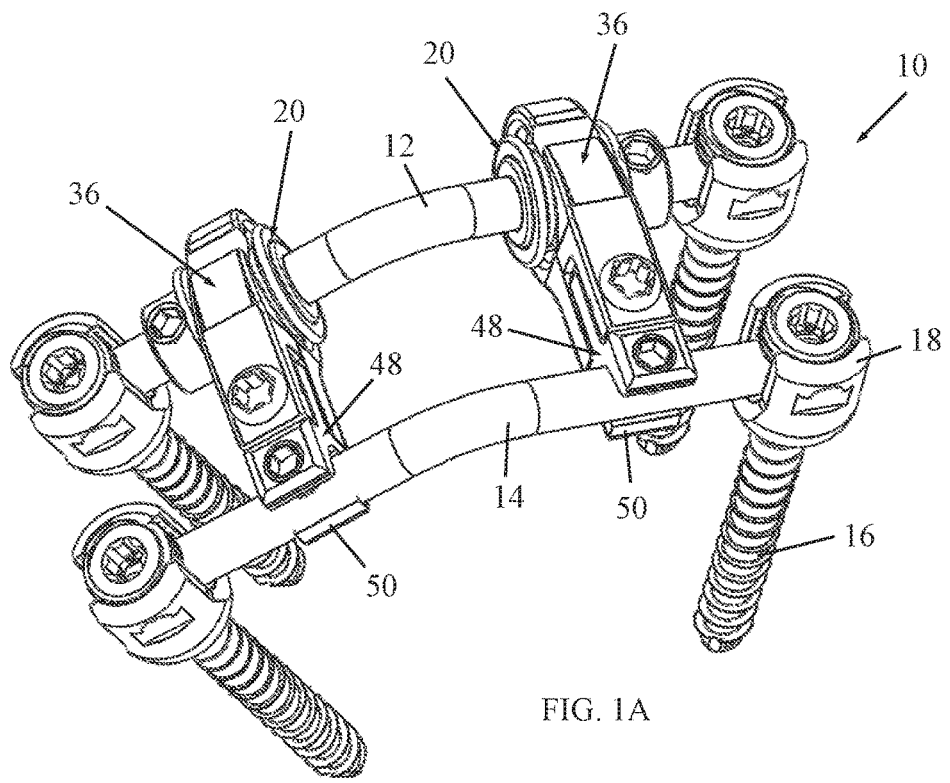
FIGS. 1A and 1B are simplified pictorial illustrations of a spinal prosthesis with one or more adjustable stopper elements, constructed in accordance with a non-limiting embodiment of the present invention, respectively attached and not attached to pedicle screws.
Figure 1B:
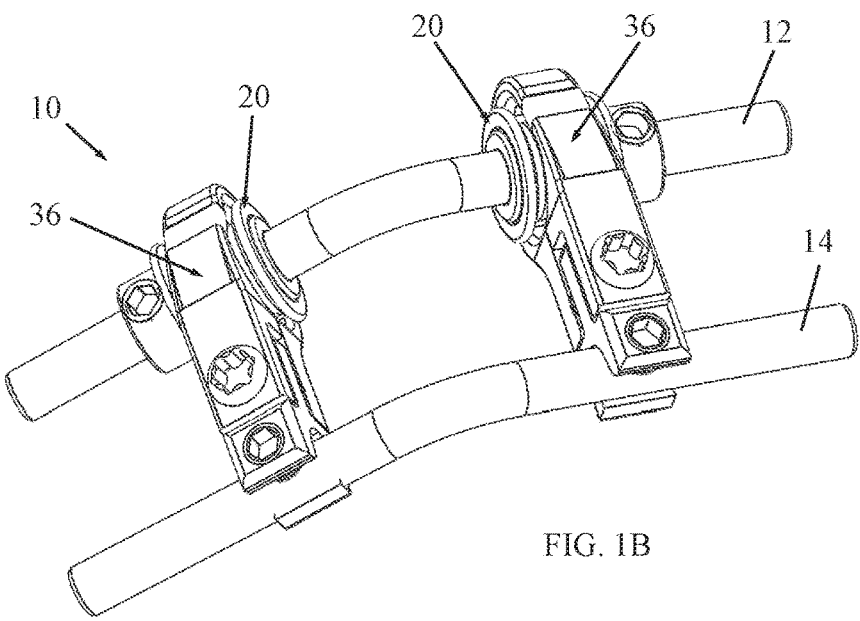
Figure 1C:
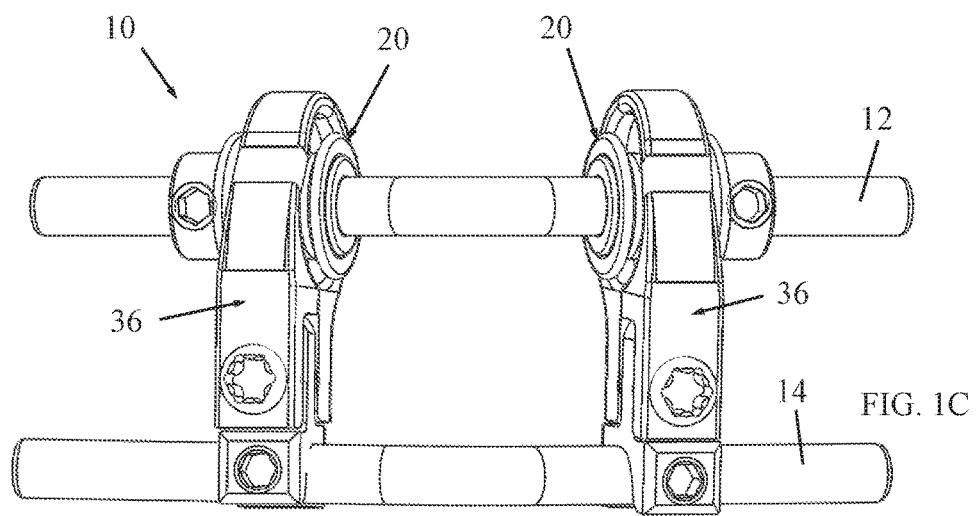
FIG. 1C is a top view of the prosthesis of FIG. 1B.

Reference is now made to FIGS. 1A-1C, which illustrate a spinal prosthesis 10, constructed and operative in accordance with an embodiment of the present invention.

Spinal prosthesis 10 may include a first spinal attachment member 12 attachable to a first spinal structure (e.g., the pedicles of the L4 vertebra), and a second spinal attachment member 14 attachable to a second spinal structure (e.g., the pedicles of the L5 vertebra). The first and second spinal structures may be adjacent superiorly-inferiorly to one another (as in the example given above, L4 and L5). Thus, first and second spinal attachment members 12 and 14 may serve as cephalad and caudal attachment members, respectively.

In the non-limiting illustrated embodiment, first and second spinal attachment members 12 and 14 include elongate members (e.g., crossbars or rods of any cross-sectional shape, such as circular or prismatic) that can be connected to the spinal structure with pedicle screws 16 provided with polyaxial heads 18. The elongate members may be straight or curved. The elongate members may have flattened areas at some point along their lengths.

Figure 2:
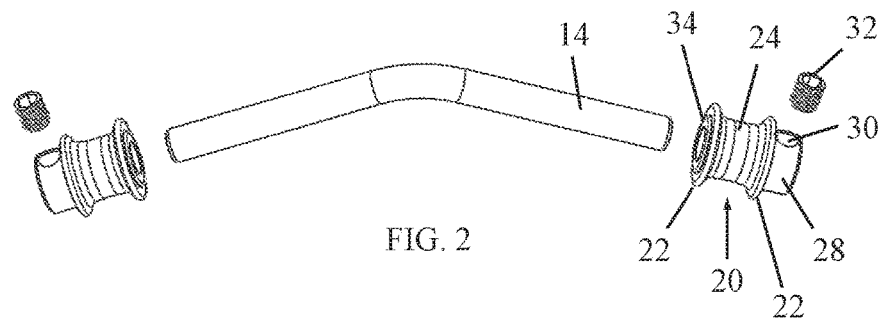
FIG. 2 is a simplified exploded illustration of adjustable stopper elements for assembling on the spinal prosthesis.

An adjustable stopper element 20 is assembled on one or both of first and second spinal attachment members 12 and 16. In the illustrated embodiment, there are two adjustable stopper elements 20 mounted on first spinal attachment member 12 and none on second spinal attachment member 14. FIG. 2 shows the possibility of two adjustable stopper elements 20 mounted on second spinal attachment member 14. Any combination of one or more adjustable stopper elements 20 on first and/or second spinal attachment members 12 and 14 is in the scope of the invention.

Figure 3A:
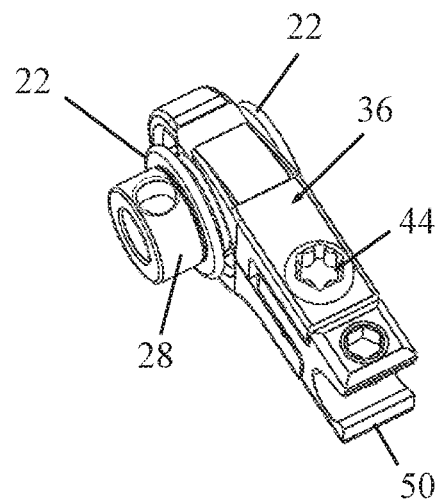
FIGS. 3A and 3B are pictorial and exploded illustrations, respectively, of the adjustable stopper element installed in a crossbar connector element, in accordance with a non-limiting embodiment of the present invention.
Figure 3B:
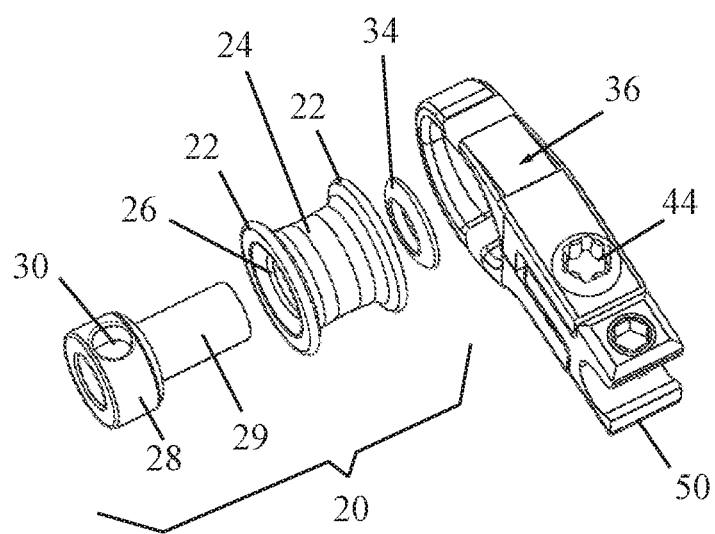

Reference is now made to FIGS. 2, 3A and 3B. The adjustable stopper element 20 includes concave end faces 22 at opposite ends of a central shaft 24. A bore (such as a central bore) 26 (FIG. 3B) is formed through the adjustable stopper element 20. The central bore 26 may be circular or may be D-shaped or other key-shapes, such as in the case of the elongate members having flattened areas. The adjustable stopper element 20 may include a mounting provision 28, such as a cylindrical hub with a bore formed therethrough, from which extends a hollow tube 29 (FIG. 3B). Mounting provision 28 may be formed with a transverse tapped hole 30 for accepting therein a fastener 32 (FIG. 2), such as an Allen screw. The opposite end of the tube 29 may be secured in shaft 24 with a tube fastener 34, such as but not limited to, a washer press fit into the end of shaft 24, or a circlips and the like. The adjustable stopper element 20 may be affixed at any point along the spinal attachment member by tightening fastener 32 through the tapped hole 30 of mounting provision 28.

An alternative construction of mounting provision 28 may be a cylindrical flange, which extends from an end of shaft 24 adjacent one of the end faces 22; there would be no tube 29 or tube fastener 34. The cylindrical flange would be formed with transverse tapped hole 30.

Figure 3C:
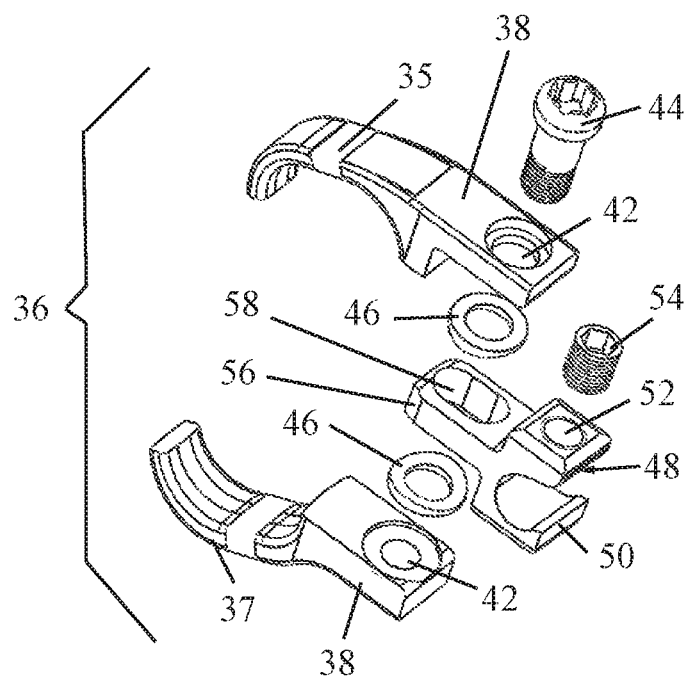
FIGS. 3C, 3D and 3E are exploded, top view and sectional illustrations, respectively, of the crossbar connector element, with FIG. 3E being taken along lines E-E in FIG. 3D.
Figure 3D:
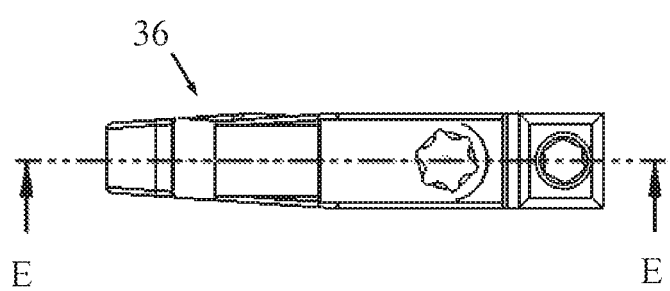
Figure 3E:
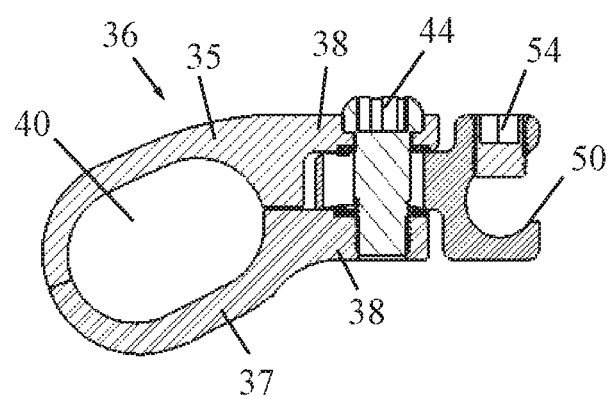

Reference is now made to FIGS. 3A-3E. A connector element 36 may be provided for assembling on adjustable stopper element 20 and the first and second spinal attachment members 12 and 14. Connector element 36 may include a first aperture-forming member 35 and a second aperture-forming member 37, each of which extends from a flange 38. Both aperture-forming members 35 and 37 are tilted with respect to their respective flange 38, as seen in FIG. 3E. When first and second aperture-forming members 35 and 37 are clamped together, they form an aperture 40 for receiving therein the shaft 24 of adjustable stopper element 20 (FIG. 3A). Although aperture 40 may be circular, in the preferred embodiment, aperture 40 is elongate or oval to provide greater freedom of movement for the first and second spinal attachment members 12 and 14 (FIG. 1A).

Range 38 may be formed with a tapped hole 42 for accepting a fastener 44 (such as a screw), which may be used with washers 46 to clamp first and second aperture-forming members 35 and 37 together (FIG. 3C). The clamp members 34 may be secured to one another by a fastener 36 (e.g., screw) that passes through hole 38 formed in first connector portion 30 and threadingly mates with a tapped hole 40 formed in second connector portion 32.

Connector element 36 may include a crossbar link member 48, which may be used to grasp and hold one of the spinal attachment members, such as the second spinal attachment member 14 as seen in FIG. 1A. As seen in FIG. 3C, crossbar link member 48 may include a grasping portion 50 shaped to match the outer contour of the spinal attachment member. The grasping portion 50 may be formed with a tapped hole 52 for accepting therein a fastener 54, such as an Allen screw, which can be tightened on the outer contour of the spinal attachment member. Crossbar link member 48 may include a flange 56 that extends from grasping portion 50, which may be formed with an elongate hole 58. The fastener 44 passes through elongate hole 58. In this manner, crossbar link member 48 is attached to the rest of connector element 36, and due to the elongate hole 58, can be adjusted to different positions with respect to the rest of connector element 36. Grasping portion 50 can be moved outwards and inwards and can also be rotated about different axes with respect to the rest of connector element 36. The adjustment of grasping portion 50 allows the surgeon to accommodate the device to different interpedicular distances (IPDs) of different patients.

In summary, the position of the adjustable stopper element 20 along first and second spinal attachment members 12 and 14 is adjustable to suit any anatomy and there is no need to perform a laminectomy. For example, adjustable stopper element 20 may be positioned on the left side of the first (upper) spinal attachment member 12 but not on the right side; conversely, another adjustable stopper element 20 may be positioned on the right side of the second (lower) spinal attachment member 14 but not on the left side. This may help in avoiding the spinous process from interfering with the prosthesis and thus avoid the need for a laminectomy.

In general, the adjustable stopper element 20 may be positioned on either side or both sides of one or both of the first and second spinal attachment members 12 and 14. Each spinal attachment member can slide relative to the adjustable stopper element 20. Once the mounting provision 28 is tightened and secured on the spinal attachment member, there is no more relative movement between the adjustable stopper element 20 and the spinal attachment member. Thus, the mounting provision 28 is structure that limits relative movement between the one or more adjustable stopper elements and the spinal attachment member on which the one or more adjustable stopper elements are mounted. Alternative or additional structure for limiting this relative movement may be provided. For example, since the adjustable stopper element 20 is straight but the spinal attachment member is not straight, the adjustable stopper element 20 will seize on the spinal attachment member and thereby prevent further sliding of the spinal attachment member relative to the adjustable stopper element 20. Additionally or alternatively, the central bore 26 of adjustable stopper element 20 may be non-straight (e.g., curved) so that the adjustable stopper element 20 will seize on the spinal attachment member even if the spinal attachment member is straight. Additionally or alternatively, the central bore 26 or the spinal attachment member may be roughened (e.g., knurled) to increase friction between the adjustable stopper element 20 and the spinal attachment member so that adjustable stopper element 20 limits relative movement of the spinal attachment member.

A typical procedure may consist of a posterior incision into the area adjacent to the affected vertebrae, without any laminectomy, insertion of pedicle screws (or even reuse of pedicle screws from another procedure such as fusion) and the implantation of spinal prosthesis 10 by the pedicle screws 16 to pedicles or other available bone structure.

Figure 4A:
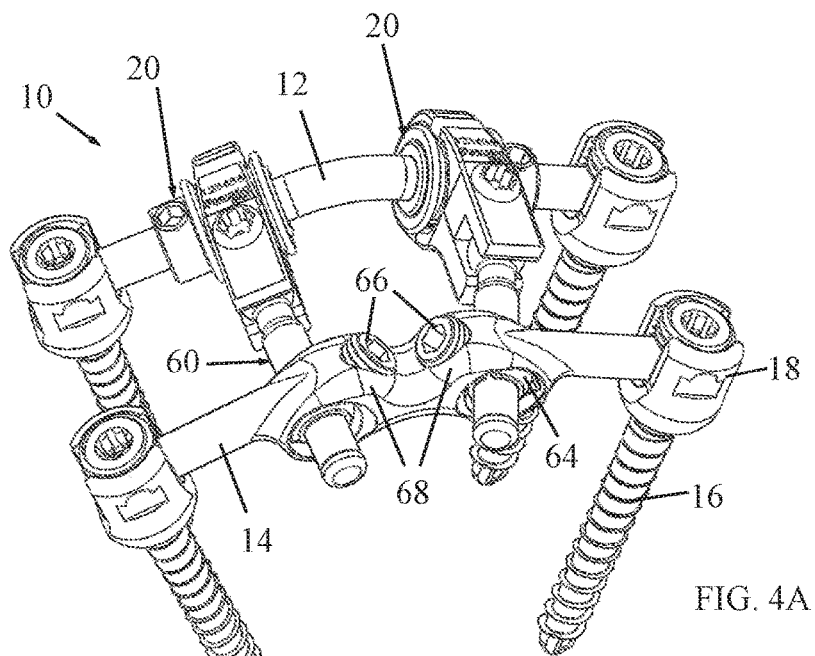
FIGS. 4A and 4B are simplified pictorial and top-view illustrations, respectively, of the spinal prosthesis and adjustable stopper elements, constructed in accordance with a non-limiting embodiment of the present invention, with a spherical-head, superior-inferior link member attached to the crossbar connector element and to a crossbar assembly.
Figure 4B:
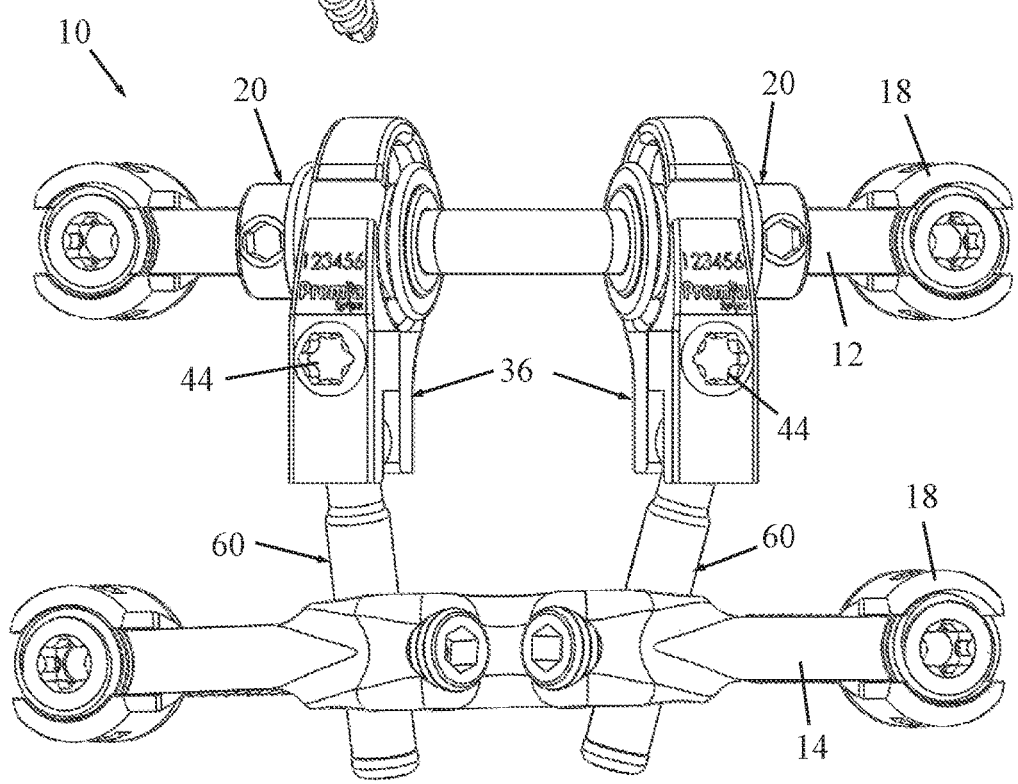
Figure 4C:
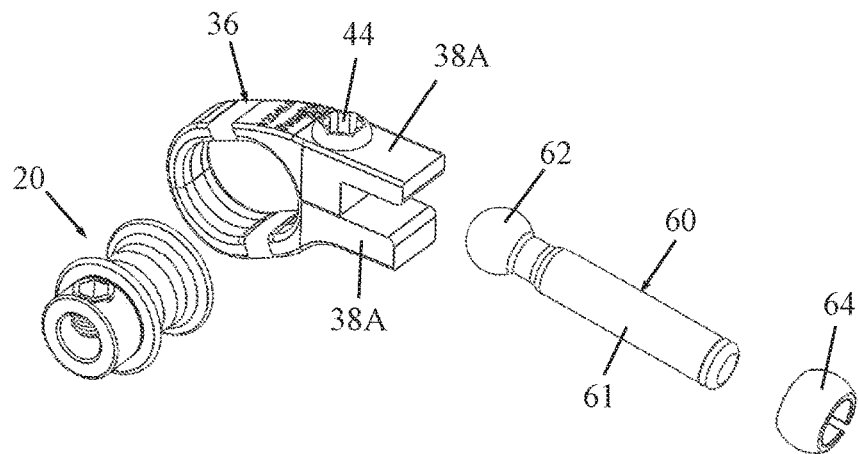
FIGS. 4C, 4D and 4E are simplified exploded, side-view and sectional illustrations, respectively, of the spherical-head, superior-inferior link member and crossbar connector element, with FIG. 4D being taken along lines D-D in FIG. 4E.
Figure 4D:
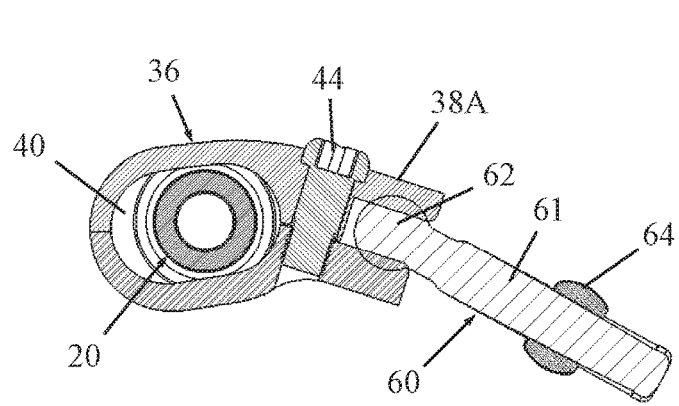
Figure 4E:
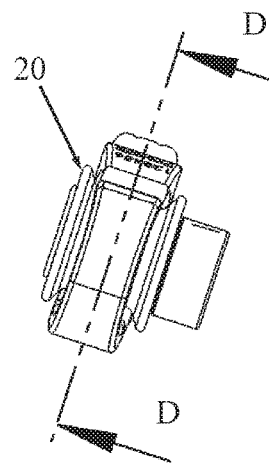

Reference is now made to FIGS. 4A and 4B, which illustrate the spinal prosthesis 10 and adjustable stopper elements 20, constructed in accordance with another non-limiting embodiment of the present invention. In this embodiment, the connector element 36 includes a modified flange 38A to which is attached a spherical-head, superior-inferior link member 60, as shown in more detail in FIGS. 4C-4E.

The link member 60 includes a shaft 61, from which extends a spherical head 62. The spherical head 62 is clamped between flanges 38A, which may be formed with semi-spherical recesses to accept the spherical head 62. A bearing element 64, such as a snap-ring with a spherical contour (thus serving as a ball bearing), may be mounted at any position along the length of shaft 61. As seen in FIG. 4A, bearing element 64 may be clamped by a fastener 66 onto the second spinal attachment member 14. The fastener 66 may pass through an angled mounting hub 68; the tilt of angled mounting hub 68 provides a low profile for minimizing the incision length needed to install the prosthesis.

Figure 5A:
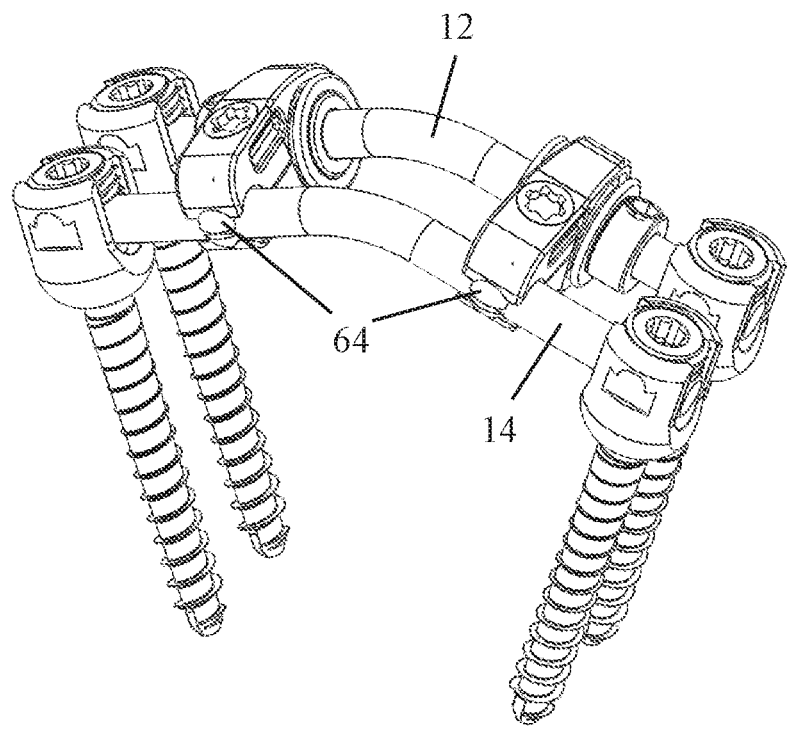
FIGS. 5A and 5B are simplified pictorial illustrations of the spinal prosthesis and adjustable stopper elements, constructed in accordance with another non-limiting embodiment of the present invention, with a bearing (e.g., ball bearing) on the inferior crossbar that allow the connector elements to rotate around the crossbar.
Figure 5B:
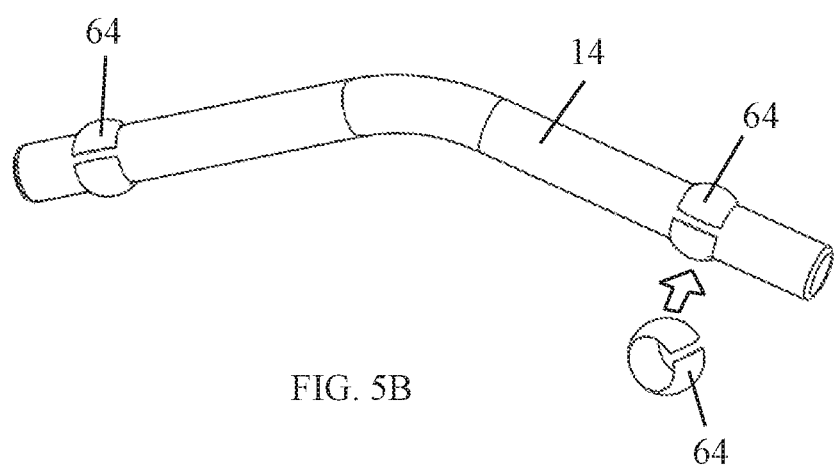
Figure 5C:
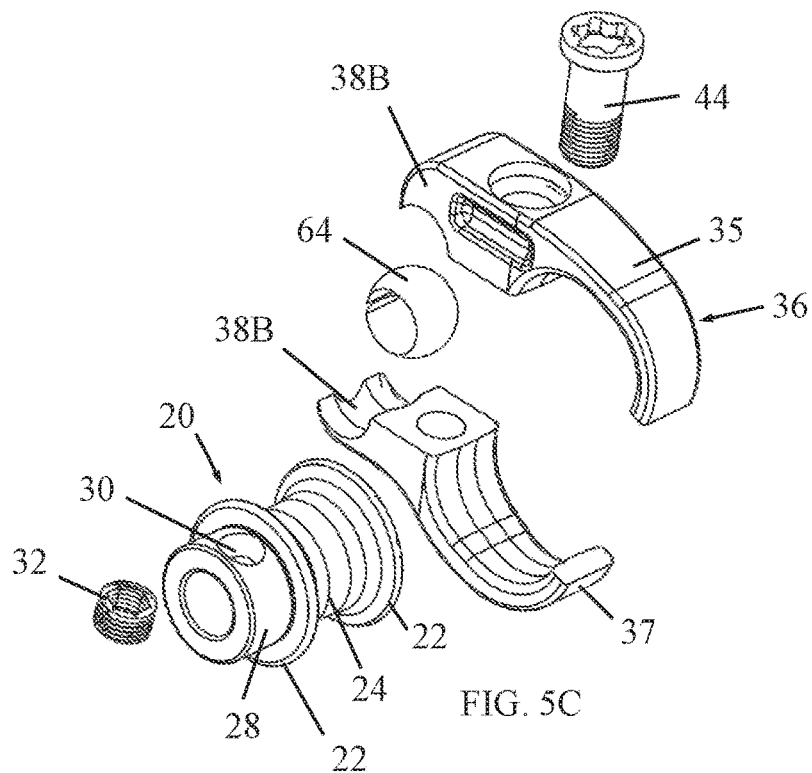
FIGS. 5C, 5D and 5E are simplified exploded, top-view and sectional illustrations, respectively, of the bearing and crossbar connector element, with FIG. 5E being taken along lines E-E in FIG. 5D.
Figure 5D:
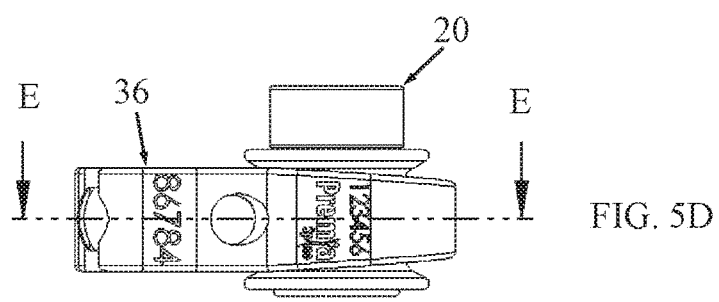
Figure 5E:
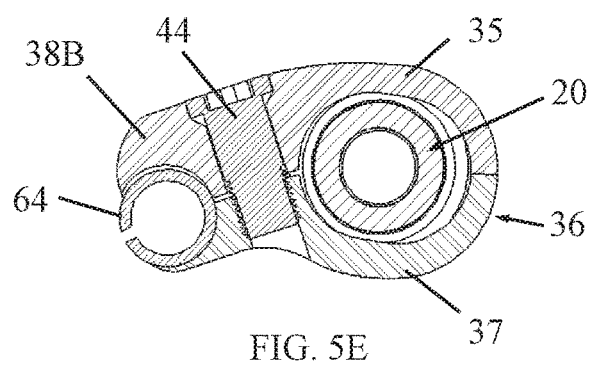

Reference is now made to FIGS. 5A-5E, which illustrate another version of the spinal prosthesis and adjustable stopper elements, constructed in accordance with another non-limiting embodiment of the present invention. In this embodiment, two bearing elements 64 are mounted on the inferior crossbar (second spinal attachment member 14), which permits the connector elements 36 to rotate around the crossbar 14. As seen in FIGS. 5C and 5E, the connector element 36 includes a modified flange 38B with rounded portions for clamping on bearing element 64.

Figure 5F:
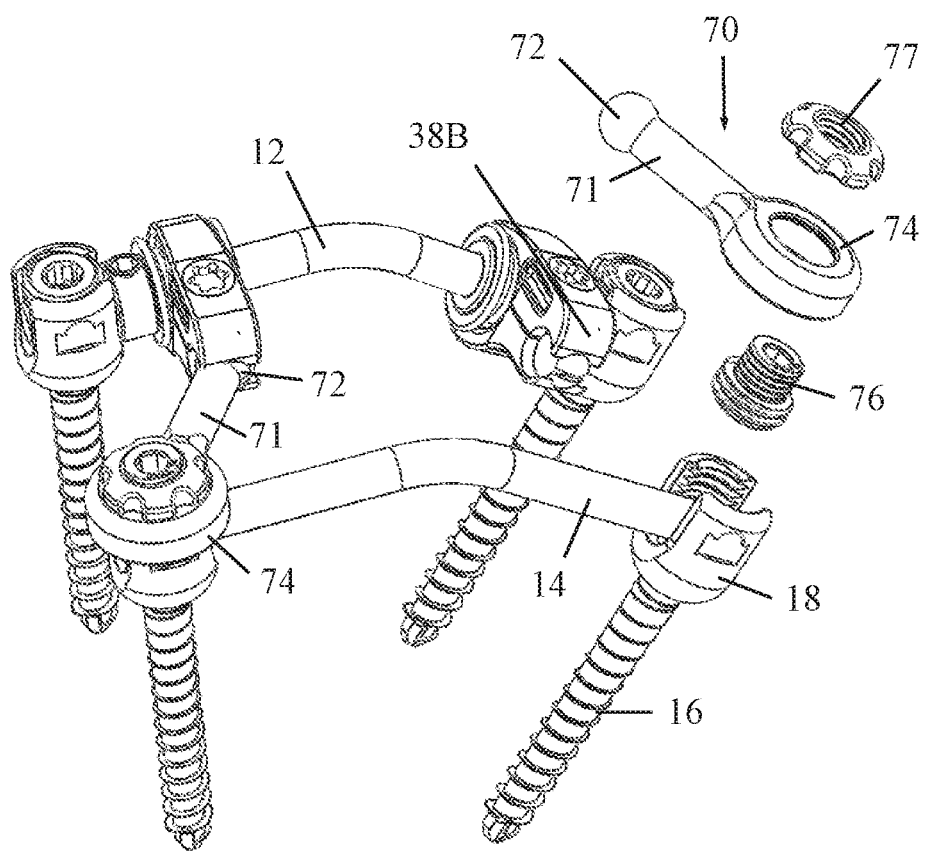
FIG. 5F is a simplified pictorial illustration of the spinal prosthesis with another spherical-head, superior-inferior link member attached to the crossbar connector element and to a pedicle screw head, in accordance with another non-limiting embodiment of the present invention.

Reference is now made to FIG. 5F. The connector element 36 with flange 38B may be used to clamp a spherical-head, superior-inferior link member 70, which includes a spherical head 72 at the end of a shaft 71. The spherical head 72 is clamped in flanges 38B. The opposite end of shaft 71 includes a pedicle-screw ring member 74, which may be secured to the head 18 of pedicle screw 16 by means of fasteners 76 and 77, such as a bolt and nut.

Reference is now made to FIGS. 6A-6C. In this embodiment, a spherical-head, superior-inferior link member 80 is attached directly to pedicle screw head 18 of pedicle screw 16, instead of to the connector element 36. Link member 80 includes a spherical head 82 which is clamped in flanges 38A of connector element 36, as similarly described above for the embodiment of FIG. 4C.

Figure 7C:
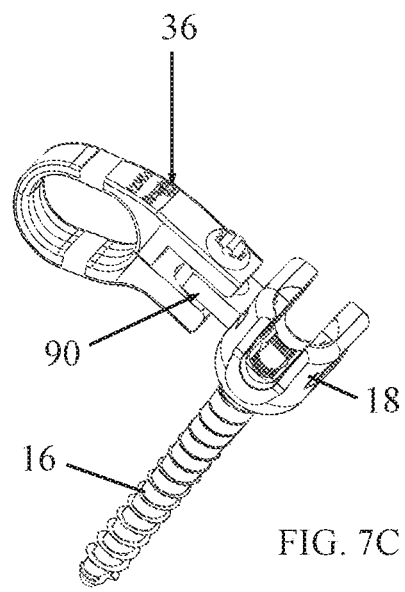
FIGS. 7B and 7C are simplified side-view and pictorial illustrations, respectively, of the link member of FIG. 7A attached to a crossbar connector element.
Figure 7B:
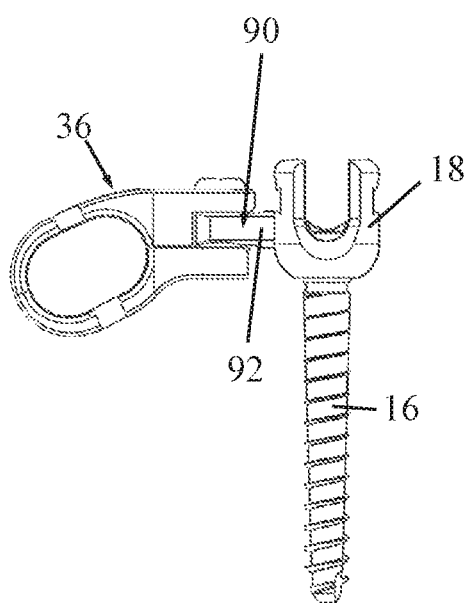
Figure 7A:
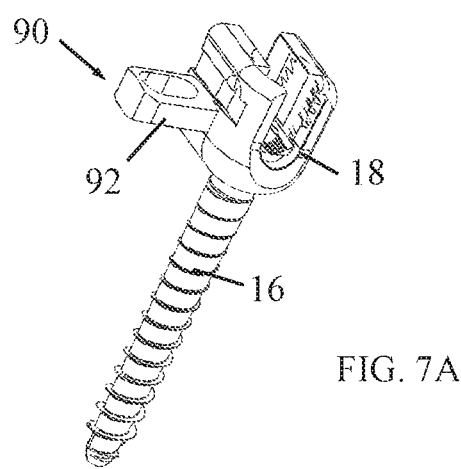
FIG. 7A is a simplified pictorial illustration of a link member attached to a pedicle screw head, in accordance with another non-limiting embodiment of the present invention.

Reference is now made to FIGS. 7A-7C. In this embodiment, a crossbar link member 90 is attached directly to pedicle screw head 18 of pedicle screw 16, instead of to the connector element 36. Link member 90 includes a flange 92 which is clamped in flanges 38 of connector element 36, as similarly described above for the embodiment of FIG. 3C.

What is claimed is:

1. A spinal prosthesis comprising:
   a first spinal attachment member;
   a second spinal attachment member;
   one or more adjustable stopper elements assembled on one or both of said first and second spinal attachment members, said one or more adjustable stopper elements being formed with a bore through which either of said first and second spinal attachment members is slidable, said one or more adjustable stopper elements comprising structure that limits relative movement between said one or more adjustable stopper elements and the spinal attachment member on which said one or more adjustable stopper elements are mounted;
   a connector element assembled on at least one of said one or more adjustable stopper elements and said first and second spinal attachment members, said connector element comprising first and second aperture-forming members, wherein said first and second aperture-forming members, when clamped together, form an aperture for receiving therein said adjustable stopper element; and
   a bearing element mounted on said second spinal attachment member, said bearing element comprising a ring with a spherical outer contour interrupted by a slit to form a partial ring, and wherein said connector element comprises a flange coupled to said bearing element, said flange comprising left and right partially-circular portions and a central partially-circular portion extending between said left and right partially-circular portions, said central partially-circular portion having a radius greater than radii of said left and right partially-circular portions.

2. The spinal prosthesis according to claim 1, wherein said structure that limits the relative movement comprises a mounting provision extending from each of said one or more adjustable stopper elements and a fastener configured to secure said mounting provision to one of said first and second spinal attachment members.

3. The spinal prosthesis according to claim 2, wherein said mounting provision comprises a hub with a bore formed therethrough, from which extends a hollow tube.

4. The spinal prosthesis according to claim 1, wherein each of said one or more adjustable stopper elements comprises a central shaft with concave end faces at opposite ends thereof, wherein a bore is formed through said adjustable stopper element.

5. The spinal prosthesis according to claim 1, wherein each of said first and second aperture-forming members extends from said flange.

6. The spinal prosthesis according to claim 5, wherein each of said first and second aperture-forming members is tilted with respect to said flange.

7. The spinal prosthesis according to claim 1, wherein said aperture for receiving therein said adjustable stopper element is elongate or oval.

8. The spinal prosthesis according to claim 1, wherein said connector element comprises a crossbar link member attached to one of said first and second spinal attachment members.

9. The spinal prosthesis according to claim 8, wherein said crossbar link member is adjustable to different positions with respect to rest of said connector element.

10. The spinal prosthesis according to claim 8, wherein said crossbar link member comprises a spherical head.

11. The spinal prosthesis according to claim 8, wherein said crossbar link member is attached to one of said first and second spinal attachment members via said bearing element.

12. The spinal prosthesis according to claim 8, wherein said crossbar link member comprises a shaft with a spherical head at one end thereof and a pedicle-screw ring member at an opposite end thereof.

13. The spinal prosthesis according to claim 8, wherein said crossbar link member extends from a pedicle screw head of a pedicle screw.

\* \* \* \* \*